United States Patent [19]

Soper

[11] Patent Number: 5,071,706
[45] Date of Patent: Dec. 10, 1991

[54] OILY, FREE-FLOWING, MICROCAPSULES

[75] Inventor: Jon C. Soper, Huber Heights, Ohio

[73] Assignee: Eurand America, Incorporated, Vandalia, Ohio

[21] Appl. No.: 401,189

[22] Filed: Aug. 31, 1989

[51] Int. Cl.[5] .................. A61K 7/46; A61K 9/50; B32B 27/00

[52] U.S. Cl. ...................... 428/402.2; 424/61; 424/455; 424/456; 424/489; 264/4.3

[58] Field of Search .............. 424/61, 455, 456, 489; 428/402.2

[56] References Cited

U.S. PATENT DOCUMENTS

| | | | |
|---|---|---|---|
| 2,491,475 | 12/1949 | Bogin | 424/453 |
| 4,500,358 | 2/1985 | Mayer et al. | 424/453 X |
| 4,777,089 | 10/1988 | Takizawa et al. | 424/455 X |
| 4,795,642 | 1/1989 | Cohen et al. | 424/455 |
| 4,832,955 | 5/1989 | Snipes et al. | 424/456 |
| 4,844,885 | 7/1989 | Chernack | 424/61 |
| 4,892,766 | 1/1990 | Jones | 424/456 X |

FOREIGN PATENT DOCUMENTS

| | | | |
|---|---|---|---|
| 0176772 | 4/1986 | European Pat. Off. | 424/455 |
| 58-138458 | 8/1983 | Japan | 424/456 |
| 0929403 | 6/1963 | United Kingdom | 424/455 |

*Primary Examiner*—Thurman K. Page
*Assistant Examiner*—Amy Hulina
*Attorney, Agent, or Firm*—Gary R. Molnar

[57] ABSTRACT

This disclosure is directed to the preparation of oily microcapsules which can be easily tray dried to a free flowing product without requiring special drying equipment. These microcapsules have a cell wall material having a first cell wall of gelatin/carboxymethylcellulose (CMC) which is prehardened (cross-linked) with a material selected from the group consisting of formaldehyde, glyoxal and glutaraldehyde to which there is grafted formaldehyde and urea. The predominant portion, viz., approximately 95% by wt. of these microcapsules have a particle size less than 1500 microns and more characteristically have a particle size ranging from about 100 to about 400 microns (microcapsular diameter). These microcapsules contain less than approximately 3 wt. % free oil and more characteristically less than about 1 wt. % free oil (non-microencapsulated oil) and have less free (unreacted) formaldehyde, which can be extracted with water, than do prior art microencapsulated oily materials. The microcapsules of this invention are granular and free-flowing when dried.

17 Claims, No Drawings

OILY, FREE-FLOWING, MICROCAPSULES

BRIEF DESCRIPTION OF THE INVENTION

This invention is directed to the preparation of oily microcapsules which can be easily tray dried to a free flowing product without requiring special drying equipment. These microcapsules have a cell wall material having a first cell wall of gelatin/carboxymethylcellulose (CMC) which is prehardened (cross-linked) with a material selected from the group consisting of formaldehyde, glyoxal and glutaraldehyde to which there is grafted formaldehyde and resorcinol which is then crosslinked with formaldehyde and urea. The predominant portion, viz., approximately 95% by wt. of these microcapsules have a size less than 1500 microns and more characteristically have a particle size ranging from about 100 to 400 microns (microcapsular diameter). These microcapsules contain less than approximately 3 wt. % free oil and more characteristically less than about 1 wt. % free oil (non-microencapsulated oil) and have less free (unreacted) formaldehyde, which can be extracted with water, than do prior art microencapsulated oily materials. The microcapsules of this invention are granular and free-flowing when dried.

BACKGROUND OF THE INVENTION AND PRIOR ART

There long has been a desire in the deodorant and cosmetic industry for a dry, aesthetically pleasing product which is substantially non-toxic and free flowing, and can be impregnated, coated and otherwise delivered to various substrates and formulations for use in various and sundry products.

There have been various attempts in the prior art to arrive at such free flowing, easily formulating products. For example, the 3M Company in its encapsulated products/3M Product Information Bulletin, entitled "3M Microcapsules Mineral Oil/180 Microns" bearing a number of 77-9802-7051-4 describes a microencapsulated mineral oil, which microcapsules are reported to have a diameter of 180 microns and are described as soft clumps of grainy, white powder with a slightly grainy feel. The microencapsulated core material is USP grade mineral oil and when pressure is applied the microcapsules break and mineral oil is released. This product has clumps or agglomerates of individual microcapsules and is stated to contain a maximum of 12 weight percent of free (non-microencapsulated) mineral oil. This product also contains 400 parts per million (maximum) of aqueous extractable formaldehyde. This product bulletin also includes the further designation of "Resin FDA CRNCS No. R0012291". The microencapsulating cell wall material, or shell material, is a urea-formaldehyde resin. The material corresponding to this 3M Product Information Bulletin does not have the free-flowing characteristics of the microcapsules produced in accordance with this invention.

U.S. Pat. No. 4,808,408, issued to R. W. Baker, is directed to preparation of microencapsulated hydrophobic materials, including fragrances. Also there is disclosed in Example 5 use of a "Gantrez" resin as a pharmaceutical vehicle to produce a resulting cream containing insect repellant.

U.S. Pat. No. 4,082,688, issued to S. Egawa, is directed to a process for producing microcapsules having a gelatin cell wall material wherein the microcapsule wall is produced by coacervation and hardened using at least two kinds of chemical hardening agents in a hardening step(s).

U.S. Pat. No. 3,691,270, issued to R. Charle et al. is directed to microencapsulation of make-up removing or treating compositions which are incorporated into a cosmetic cream or incorporated in a flexible support described as an aloe vera polymer support.

U.S. Pat. No. 4,205,060, issued to H. G. Monsimer, teaches in its Example 5 use of hydrolyzed "Gantrez AN169" copolymer of methyl vinyl ether and maleic anhydride to microencapsulate medicaments.

It will be clearly evident that the microcapsules of the present invention possess a desirable combination of properties not possessed by the prior art patents and the product bulletin referred to above.

DETAILED DESCRIPTION OF THE INVENTION

The microcapsules of the present invention are characterized as being free-flowing and substantially free from clumps and agglomerates of individual microcapsules. The predominant portion of these microcapsules, viz., about 95 wt. % have a particle size of less than about 1500 microns and more characteristically about 100 to 400 microns. Moreover, these oily core microcapsules are readily tray driable, readily formulatable and contain a maximum of approximately 3 wt. % free oil and more characteristically less than about 1 wt. % free (non-microencapsulated) oil and contain less free formaldehyde, viz., that which can be extracted with water, than prior art microencapsulated products.

The analytical procedure used for free oil analysis is not capable of determining free oil with highly volatile microcapsule core materials, such as fragrance oils.

A variety of core materials can be employed to form the microcapsules in accordance with the present invention. Suitable core materials of an oily nature which can be employed in the present invention include, but are not necessarily limited to, the following: mineral oil, and other lubricant oils, emollients, fragrance oils, escalol and other oily sunscreen materials, aloe vera, silicone oil, jojoba oil, esters of vitamin E, such as vitamin E acetate, vitamin E linoleate, vitamin E palmitate, vitamin A, menthol eucalyptus formulations, fruit oils, e.g., lemon oil, citrus base fragrance oil, and other citrus fragrances, oily color producing materials, etc.

The microencapsulating cell wall materials employed in accordance with this invention result in what is believed to be a basic microcapsule cell wall of gelatin/carboxymethylcellulose (CMC) prehardened with a material selected from the group consisting of formaldehyde, glyoxal and glutaraldehyde and grafted with formaldehyde and resorcinol and cross linked with formaldehyde and urea. Whether this results (A) in two separate and discrete microcapsule walls, the interior one being the gelatin/CMC polymer and the outer microcapsular cell wall being the resorcinol-formaldehyde/urea formaldehyde resin, or (B) in one microcapsular wall of mixed composition is not clearly understood.

It is believed, however, that the resorcinol-formaldehyde/urea formaldehyde polymer forming components of the cell wall(s) react(s) with the gelatin/CMC cell wall previously formed and prevents the weeping of the oily core material therefrom while strengthening the initially formed microcapsule gelatin/CMC wall and makes it sufficiently strong to withstand the rigors of processing, such as washing, drying, sieving and packaging. Also, it is believed that the resorcinol, formaldehyde/urea, formaldehyde polymer former complex with the hydrophilic groups on the gelatin-containing initially formed polymer cell wall and shrink it while hardening same thereby enabling the aesthetically desired small microcapsule size to be obtained in conjunction with the very low concentration of free oily core material while avoiding the formation of agglomerates or clumps of microcapsules such as is encountered in some prior art products. The present invention is not dependent for successful operation on this or any other theory however.

The present invention will be illustrated in greater detail in the example which follows:

EXAMPLE (Microencapsulation of citrus base fragrance oil to produce free flowing, talc type microencapsulated deodorant product)

200 grams of 10% weight percent aqueous gelatin solution at 40 degrees C. are combined with 600 grams of distilled water at 40 degrees C. in a mixing tank. Then 200 grams of the internal phase citrus base fragrance oil core material at 30 degrees to 40 degrees C. are milled into the gelatin/water previously added to produce the particle size core material of 150 microns peak size distribution. The pH of this mix is adjusted with a 20 weight % aqueous solution of sodium hydroxide to a pH of 5.0 to 5.1.

Then there is added 80 grams of a two percent by weight aqueous solution containing carboxymethyl cellulose.

Then the preparation is cooled slowly from 40 degrees C. to a temperature of 30 degrees C. over a 30 to 40 minute period. The pH of this preparation is then adjusted to a pH of 4.8 at 29.5 degrees C. using 10% by weight aqueous acetic acid solution for pH adjustment and slow cooling to 28 degrees C. is continued for about 10 minutes.

The preparation is then prehardened using 5 cc's of a 25 weight percent aqueous solution of glutaraldehyde.

POST TREATMENT

After permitting the preparation to stand for about 2 hours, there is added thereto a polyvinyl alcohol solution consisting of 5 weight percent aqueous solution of duPont "Evanol 71/30" in an amount of 12 cc's.

This preparation is then stirred for 10 minutes and the pH thereof is adjusted to approximately 3 with a 10% by weight aqueous sulfuric acid solution using approximately 10–12 ml thereof for this purpose. After stirring said preparation for 5 minutes, 12.7 cc of a 37 weight percent aqueous formaldehyde solution is added. Then the preparation is stirred continuously for 5 minutes whereupon 11.2 grams of resorcinol predissolved in 20 cc of water is added to the preparation in a small amount of water.

Then the preparation is stirred for 1 hour whereupon 37.5 cc's of a 37 weight percent aqueous formaldehyde solution is added, following by stirring for 5 minutes. Then 18.8 grams of urea predissolved in 30 ml of water is added to the preparation. This preparation is then stirred for one hour, after which the pH is adjusted to 1.4 using a 10 weight percent aqueous solution of sulfuric acid. This preparation is then stirred for from 6 to 16 hours. The microencapsulated fragrance oil formulation is then washed twice with approximately equal volumes of water, followed by neutralization to a pH of 5.5 to 4.5 using 20 wt. % aqueous sodium hydroxide solution to accomplish this pH adjustment.

After this, the washed, neutralized microcapsules are Buchner filtered and dried using a tray dryer.

The resulting citrus base fragrance oil microcapsules have a peak particle size distribution of 150 microns (microcapsule diameter) and were substantially free of clumps and agglomerates. The percent free fragrance oil of these microcapsules could not be determined due to the high volatility of this core material. The free formaldehyde present in these dried microcapsules was determined to be less than 10 parts per million by aqueous extraction.

Due to their free flowing nature and the substantial freedom from clumps and agglomerates of individual microcapsules, the oily core microcapsules of this invention having microcapsular cell wall material of gelatin/carboxymethyl cellulose prehardened with a material selected from the group consisting of formaldehyde, glyoxal and glutaraldehyde and having grafted thereto formaldehyde and resorcinol and crosslinked with formaldehyde and urea and having approximately 95% by weight having a particle between about 100 microns and about 400 microns and are well suited to the preparation of aqueous formulations containing said microcapsules.

These aqueous formulations characteristically contain from about 10 to about 40 weight % of said microcapsules with the remainder being water and formulation aids. Such aqueous formulations can be used to impregnate, coat or otherwise deliver said microcapsules to woven and non-woven fabric substrates; rubber, plastic and other polymer foam structures; paper, etc. These aqueous formulations can be made from the dried microcapsules or by tailor making them without drying by use of the desired amount of water.

The oily core microcapsules in such aqueous formulations characteristically have a particle size peak distribution of about 150 microns.

I claim:

1. Microencapsulated product having a predominant portion of individual microcapsules having a particle size less than about 1500 microns and containing oil core material, said microencapsulated product being free-flowing, having a free oil concentration less than about 3 wt. %, and being further characterized as substantially free of clumps and agglomerates of individual microcapsules and containing microcapsular cell wall material of gelatin/carboxymethylcellulose prehardened with a material selected from the, group consisting of formaldehyde, glyoxal and glutaraldehyde treated with polyvinyl alcohol and having grafted thereto formaldehyde and resorcinol and crosslinked with formaldehyde and urea.

2. Microencapsulated product as in claim 1 wherein said oil core material contains emollient.

3. Microencapsulated product as in claim 1 wherein said oil core material contains lubricant.

4. Microencapsulated product as in claim 1 wherein said oil core material contains mineral oil.

5. Microencapsulated product as in claim 1 wherein said microcapsule particle size ranges from about 100 microns to about 400 microns.

6. Microencapsulated product having a predominant portion of individual microcapsules having a particle size less than about 1500 microns and containing fragrance oil core material, said microencapsulated product being free-flowing and being further characterized as substantially free of clumps and agglomerates of individual microcapsules and containing microcapsular cell wall material of gelatin/carboxymethylcellulose prehardened with a material selected from the group consisting of formaldehyde, glyoxal and glutaraldehyde treated with polyvinyl alcohol and having grafted thereto formaldehyde and resorcinol and crosslinked with formaldehyde and urea.

7. Microencapsulated product as in claim 6 wherein said fragrance oil contains citrus base fragrance oil.

8. Microencapsulated product as in claim 1 wherein said microcapsules have a particle size peak distribution of about 150 microns.

9. A process of producing the microencapsulated product of claim 1 which comprises microencapsulating an oil core material with a microcapsule cell wall system of gelatin/carboxymethylcellulose, prehardening same with a material selected from the group consisting of formaldehyde, glyoxal and glutaraldehyde and thereafter treating with polyvinyl alcohol and grafting to the initially formed microcapsule cell wall material formaldehyde and resorcinol and subsequently crosslinking with formaldehyde and urea.

10. A process of producing the microencapsulated product of claim 6 which comprises microencapsulating an oily core material containing fragrance oil with a microcapsule cell wall system of gelatin/carboxymethylcellulose, prehardening same with a material selected from the group consisting of formaldehyde, glyoxal and glutaraldehyde and thereafter grafting to the initially formed microcapsule cell wall material formaldehyde and resorcinol and subsequently crosslinking with formaldehyde and urea.

11. Aqueous formulations containing from about 10 to about 40 wt. % of individual microcapsules, having a particle size ranging from about 100 to about 400 microns and being substantially free of clumps and agglomerates of individual microcapsules, containing oil core material and containing microcapsular cell wall material of gelatin/carboxymethylcellulose prehardened with a material selected from the group consisting of formaldehyde, glyoxal and glutaraldhyde treated with polyvinyl alcohol and having grafted thereto formaldehyde and resorcinol and crosslinked with formaldehyde and urea, with the remainder being water and formulation aids.

12. Aqueous formulations as in claim 11 wherein said oil core material contains fragrance oil.

13. Aqueous formulations as in claim 11 wherein said oil core material contains color producing material.

14. Aqueous formulations as in claim 11 wherein said oil core material contains lubricant.

15. Aqueous formulations as in claim 11 wherein said oil core material contains citrus base fragrance oil.

16. Aqueous formulations as in claim 11 wherein said oil core material contains an emollient.

17. Aqueous formulations as in claim 11 wherein said microcapsules have a particle size peak distribution of about 150 microns.

* * * * *